US009927399B2

United States Patent
Shimura et al.

(10) Patent No.: US 9,927,399 B2
(45) Date of Patent: Mar. 27, 2018

(54) CAPILLARY DEVICE FOR SEPARATION AND ANALYSIS, MICROFLUIDIC CHIP FOR SEPARATION AND ANALYSIS, ANALYSIS METHOD FOR PROTEINS OR PEPTIDES, ELECTROPHORESIS INSTRUMENT, AND MICROFLUIDIC CHIP ELECTROPHORESIS INSTRUMENT FOR SEPARATION AND ANALYSIS

(71) Applicants: FUKUSHIMA MEDICAL UNIVERSITY, Fukushima (JP); NICHIEI INDUSTRY CO., LTD., Tokyo (JP)

(72) Inventors: Kiyohito Shimura, Fukushima (JP); Toshihiko Nagai, Fukushima (JP); Shuuichi Fukuhara, Fukushima (JP); Yoshi-ichi Seto, Fukushima (JP)

(73) Assignees: NICHIEI INDUSTRY CO., LTD., Tokyo (JP); Kiyohito Shimura, Fukushima (JP)

( * ) Notice: Subject to any disclaimer, the term of this patent is extended or adjusted under 35 U.S.C. 154(b) by 126 days.

(21) Appl. No.: 15/025,809

(22) PCT Filed: Oct. 14, 2014

(86) PCT No.: PCT/JP2014/077340
§ 371 (c)(1),
(2) Date: Mar. 29, 2016

(87) PCT Pub. No.: WO2015/072265
PCT Pub. Date: May 21, 2015

(65) Prior Publication Data
US 2016/0245778 A1    Aug. 25, 2016

(30) Foreign Application Priority Data
Nov. 12, 2013   (JP) .................. 2013-234146

(51) Int. Cl.
*G01N 27/447* (2006.01)
*C07K 1/28* (2006.01)
*G01N 30/00* (2006.01)

(52) U.S. Cl.
CPC ......... *G01N 27/44795* (2013.01); *C07K 1/28* (2013.01); *G01N 27/44717* (2013.01);
(Continued)

(58) Field of Classification Search
CPC .................... G01N 27/44791; C07K 1/28
See application file for complete search history.

(56) References Cited

U.S. PATENT DOCUMENTS
4,680,201 A * 7/1987 Hjerten ............. B05D 7/22
                                            204/601
5,202,010 A   4/1993 Guzman
(Continued)

FOREIGN PATENT DOCUMENTS
CN    102680557 A  * 9/2012 ......... G01N 27/447
JP    H04-318453 A   11/1992
(Continued)

OTHER PUBLICATIONS

EPO computer-generated English language translation of Wu et al. CN 102680557 A. Downloaded Sep. 25, 2017.*
JPO computer-generated English language translation of JP 2006-038535 A. Downloaded Sep. 26, 2017.*
JPO computer-generated English language translation of JP 2008-038535 A. Downloaded Feb. 1, 2018.*
(Continued)

*Primary Examiner* — Alexander S Noguerola
(74) *Attorney, Agent, or Firm* — Nakanishi IP Associates, LLC

(57) ABSTRACT

A method for analyzing a protein and a peptide, includes: providing a capillary for isoelectric focusing; providing a capillary device for separation and analysis having the capillary and a solid-phase extraction column being unified as a single tube-like structure; providing an electrophoresis instrument having the capillary device and the mechanism
(Continued)

regulating the pressure difference at both ends of the capillary device; introducing a sample containing a target protein or peptide into the solid-phase extraction column to let the target protein or peptide be adsorbed on the column, and filling the capillary device with a carrier ampholyte solution; starting separation by isoelectric focusing after eluting the target protein or peptide by filling the solid-phase extraction column with electrode solution or acid or base solution, or after firstly eluting the target protein or peptide with an eluting solution containing carrier ampholyte and secondly filling the solid-phase extraction column with electrode solution or acid or base solution; and focusing the eluted target protein or peptide in the capillary for isoelectric focusing.

13 Claims, 4 Drawing Sheets

(52) U.S. Cl.
CPC . *G01N 27/44743* (2013.01); *G01N 27/44791* (2013.01); *G01N 2030/009* (2013.01)

(56) References Cited

U.S. PATENT DOCUMENTS

| | | | |
|---|---|---|---|
| 5,246,577 | A | 9/1993 | Fuchs et al. |
| 5,282,942 | A * | 2/1994 | Herrick ............ G01N 27/44752 204/454 |
| 5,340,452 | A | 8/1994 | Brenner et al. |
| 5,376,249 | A * | 12/1994 | Afeyan ............ G01N 27/44747 204/452 |
| 5,482,608 | A | 1/1996 | Keely et al. |
| 5,741,639 | A | 4/1998 | Ensing et al. |
| 2007/0014699 | A1 | 1/2007 | Ratnayake et al. |
| 2010/0006436 | A1 | 1/2010 | Oishi et al. |

FOREIGN PATENT DOCUMENTS

| | | |
|---|---|---|
| JP | H06-242073 A | 9/1994 |
| JP | H07-311198 A | 11/1995 |
| JP | H08-327594 A | 12/1996 |
| JP | 2006-038535 A | 2/2006 |
| JP | 2008-256460 A | 10/2008 |
| JP | 2008-547021 A | 12/2008 |

OTHER PUBLICATIONS

Liu, Z., Pawliszyn, J. Coupling of solid-phase microextraction and capillary isoelectric focusing with laser-induced fluorescence whole column imaging detection for protein analysis. Anal Chem. 2005;77:165-171.
Cai J, El Rassi Z. On-line preconcentration of triazine herbicides with tandem octadecyl capillaries-capillary zone electrophoresis. J Liq Chromatogr. 1992;15(6-7):1179-1192.
Guzman NA, Stubbs RJ. The use of selective adsorbents in capillary electrophoresis-mass spectrometry for analyte preconcentration and microreactions: a powerful three-dimensional tool for multiple chemical and biological applications. Electrophoresis. 2001;22(17):3602-3628.
Guzman NA, Phillips TM. Immunoaffinity CE for proteomics studies. Anal Chem. 2005;77(3):61A-67A.
Guzman NA, Blanc T, Phillips TM. Immunoaffinity capillary electrophoresis as a powerful strategy for the quantification of low-abundance biomarkers drugs and metabolites in biological matrices. Electrophoresis. 2008;29(16):3259-3278.
Guzman NA, Phillips TM. Immunoaffinity capillary electrophoresis: a new versatile tool for determining protein biomarkers in inflammatory processes. Electrophoresis. 2011;32(13):1565-1578.
Shimura K, Kitamori T. An integrated protein analysis chip: On-chip combination of immunoaffinity chromatography and isoelectric focusing. In: Viovy JL, Tabeling P, Descroix S, Malaquin L, editors. The Proceedings of μTAS 2007 Conference. Paris: 2007. p. 799-801.
Shimura K, Takahashi K, Koyama Y, Sato K, Kitamori T. Isoelectric focusing in a microfluidically defined electrophoresis channel. Anal Chem. 2008;80:3818-3823.
Maria Rowena et al., Sample enrichment techniques in cappillary electrophoresis: Focus on peptides and proteins, Journal of Chromatography B, 2006, 841, 88-95.
Luo-Hong Zhang et al., In-capillary solid-phase extraction-capillary electrophoresis for the determination of chlorophenols in water, Electrophoresis, 2006, 27, 3224-3232.
International Search Report issued in PCT/JP2014/077340, dated Jan. 27, 2015 and translation thereof (5 pages).
Written Opinion of the International Searching Authority issued in PCT/JP2014/077340, dated Jan. 27, 2015 (4 pages).
Written Opinion of the International Searching Authority issued in PCT/JP2014/077340, dated Dec. 8, 2015 (7 pages).
International Preliminary Report on Patentability (IPRP) dated Mar. 2, 2016, issued in International Patent Application No. PCT/JP2014/077340, with English translation (20 Pages).

* cited by examiner

Abbreviations

SPE column: Solid-phase extraction column
IEF: Isoelectric focusing
RS: Rinse solution
CAS: Carrier ampholyte solution
TP: Target protein
IS: Interfering substance
AS: Acid solution
PB: Pressure in balance with EOF
EOF: Electroosmotic flow
PO: Pressure overwhelming EOF

CAPILLARY DEVICE FOR SEPARATION AND ANALYSIS, MICROFLUIDIC CHIP FOR SEPARATION AND ANALYSIS, ANALYSIS METHOD FOR PROTEINS OR PEPTIDES, ELECTROPHORESIS INSTRUMENT, AND MICROFLUIDIC CHIP ELECTROPHORESIS INSTRUMENT FOR SEPARATION AND ANALYSIS

CROSS-REFERENCE TO RELATED APPLICATIONS

The present application is a national stage application under 35 U.S.C. § 371 of International Application No. PCT/JP2014/077340 filed on Oct. 14, 2014, which claims priority of Japanese Patent Application No. 2013-234146 filed on Nov. 12, 2013, which are incorporated by reference in their entirety herein.

BACKGROUND OF THE INVENTION

Field of the Invention

The invention relates to a capillary device for separation and analysis, a microfluidic chip for separation and analysis, an analysis method for proteins or peptides, an electrophoresis instrument, and a microfluidic chip electrophoresis instrument for separation and analysis.

Description of the Related Art

A protein even being originated from a single gene often exists in multiple molecular forms produced by post translational modification, such as phosphorylation, glycosylation, etc. The distribution pattern of these molecular forms is related to the regulation of the function of the protein in cells and individuals. In a view from the other side, the distribution pattern can be considered to reflect the conditions of the cells and individuals enabling to provide valuable information about the condition of the organism. As a promising method for the analysis of the pattern of the molecular forms produced by post translational modification, capillary isoelectric focusing should be noticed having high-separation ability and completing separation in a short time.

There are, however, two main issues, when a biological sample such as serum and the like is analyzed by capillary isoelectric focusing.

One issue is that highly abundant proteins such as albumin mask the target protein present at low concentration, and make it difficult to detect the target protein. Besides, highly abundant proteins precipitate during separation process and cause generation of noise at the step of detection.

Another issue is that the salts present in the sample elongate the time required for focusing during isoelectric focusing and change a separation pattern.

For these issues, in Non-patent Reference 1, as a method of analysis using a protein analysis instrument, a method to link solid-phase extraction and isoelectric focusing is proposed.

Up to now, devices aimed at the online connection of solid-phase extraction and zone electrophoresis have been proposed.

For example, in Patent Reference 1, a structure of capillary electrophoresis instrument and an online sample concentration adsorbents unified with a capillary for zone electrophoresis to be used in the above instrument were disclosed.

In Patent Reference 2, a structure of an online adsorption column that is aimed to accomplish concentration of dilute sample in capillary zone electrophoresis was proposed.

In Patent Reference 3, in capillary zone electrophoresis, online coupling with the adsorbent concentrating a low concentration sample was proposed.

In Non-patent Reference 2, using combination of a capillary for solid-phase extraction, in which octadecyl group is bound on its inner wall, with a capillary for zone electrophoresis, it is demonstrated that detection sensitivity can be improved by online separation of concentrated sample in the octadecyl-bound moiety.

Besides, in Non-patent References 3~6, the online coupling of solid-phase extraction and capillary zone electrophoresis was examined.

On the other hand, in Non-patent Reference 7~8, a microfluidic chip aiming at integration of solid-phase extraction and isoelectric focusing by means of manifold channels was disclosed. To be specific, the microfluidic microchip described in the non-patent Reference 7~8 was designed to achieve connection of the channel for isoelectric focusing to electrodes by filling the manifold channels with electrode solutions after eluting a target protein from the solid phase extraction adsorbent into the channel for isoelectric focusing.

REFERENCES FOR PRIOR ART

Patent References

Patent Reference 1: U.S. Pat. No. 5,202,010
Patent Reference 2: U.S. Pat. No. 5,246,577
Patent Reference 3: U.S. Pat. No. 5,340,452

Non-Patent References

Non-patent Reference 1: Liu, Z., Pawliszyn, J. Coupling of solid-phase microextraction and capillary isoelectric focusing with laser-induced fluorescence whole column imaging detection for protein analysis. Anal Chem. 2005; 77:165-171
Non-patent Reference 2: Cai J, El Rassi Z. On-line preconcentration of triazine herbicides with tandem octadecyl capillaries-capillary zone electrophoresis. J Liq Chromatogr. 1992; 15(6-7):1179-1192
Non-patent Reference 3: Guzman N A, Stubbs R J. The use of selective adsorbents in capillary electrophoresis-mass spectrometry for analyte preconcentration and microreactions: a powerfid three-dimensional tool for multiple chemical and biological applications. Electrophoresis. 2001; 22(17):3602-3628
Non-patent Reference 4: Guzman N A, Phillips T M. Immunoaffinity CE for proteomics studies. Anal Chem. 2005; 77(3):61A-67A
Non-patent Reference 5: Guzman N A, Blanc T, Phillips T M Immunoaffinity capillary electrophoresis as a powerful strategy for the quantification of low-abundance biomarkers drugs and metabolites in biological matrices. Electrophoresis. 2008; 29(16):3259-3278
Non-patent Reference 6: Guzman N A, Phillips T M. Immunoaffinity capillary electrophoresis: a new versatile tool for determining protein biomarkers in inflammatory processes. Electrophoresis. 2011:32(13):1565-1578
Non-patent Reference 7: Shimura K, Kitamori T. An integrated protein analysis chip: On-chip combination of immunoaffinity chromatography and isoelectric focusing. In: Viovy J L, Tabeling P, Descroix S. Malaquin L, editors. The Proceedings of μTAS 2007 Conference. Paris: 2007. p. 799-801

Non-patent Reference 8: Shimura K, Takahashi K, Koyama Y, Sato K, Kitamori T. Isoelectric focusing in a microfluidically defined electrophoresis channel Anal Chem. 2008; 80:3818-3823

The solid-phase adsorbent used in Non-patent Reference 1 was an optical fiber with a diameter of 0.34 mm having an extraction phase on the surface of its tip, and adsorbs a sample component, being immersed in a sample solution for a fixed period of time. The solid-phase adsorbent was designed to adsorb only a part of the target molecule in a sample, and was not aimed at nearly thorough capture of the target molecule. Consequently, in the case where quantitative determination is required, the factors affecting the kinetics of the adsorption reaction must be precisely controlled, i.e., the time of adsorption reaction, temperature, the viscosity of a sample solution, etc. Besides, since only a part of the target molecule is adsorbed, the sensitivity cannot be maximized. When an analysis by capillary isoelectric focusing is carried out, the solid-phase adsorbent is inserted in the insertion port with an inner diameter of 0.38 mm provided at the end of the capillary for isoelectric focusing, and electrophoresis is initiated. To use the solid-phase adsorbent, the micro-porous membrane is necessary to establish electrical connection between the capillary for isoelectric focusing and the electrode solution. This and other feature of the solid-phase adsorbent make its use incapable in a commonly available capillary electrophoresis instrument.

Besides, all the devices described in Patent Reference 1~3 and Non-patent Reference 2~6 are aimed at the coupling of solid-phase extraction and capillary zone electrophoresis, and description or suggestion about the coupling of solid-phase extraction and capillary isoelectric focusing are entirely missing. Besides, the analysis method that couples solid-phase extraction and capillary zone electrophoresis has not come to be used widely.

Besides, in Non-patent Reference 7~8, solid-phase extraction and isoelectric focusing is connected via manifold channels. To transfer all the captured sample on the solid-phase adsorbent into the isoelectric focusing channel, the sample must be eluted in a narrow zone in order that all the eluted sample zone could stay in the isoelectric focusing channel, and this, however, was not always realized easily.

In addition to this issue, to use the microfluidic chip described in Non-patent Reference 7, multiple number of micro-valves (8 valves in Non-patent Reference 7) are necessary to stop the flow at the channel ports of the chip, and, however, the manufacturing of the micro-valves with a machining accuracy enabling necessary fluidic control was difficult.

Besides, the manifold channel connecting the cathodic end of the isoelectric focusing channel and the cathode has to be filled with a base solution, such as sodium hydroxide solution. This base solution, however, accelerates the peeling of the neutral polymer coating that is attached on the inner wall of the chip channel to suppress electroosmosis. This makes it difficult to perform multiple analysis for the examination of reproducibility.

This invention was made in consideration of the above mentioned situation and provides a capillary device for separation and analysis, a microfluidic chip for separation and analysis, an analysis method for proteins and peptides, an electrophoresis instrument, and a microfluidic chip electrophoresis instrument, all of which lead to an easy and highly sensitive analysis of proteins and peptides. The inventors assiduously addressed the above mentioned issues, and completed this in by unifying a solid-phase extraction column and a capillary for isoelectric focusing.

SUMMARY OF THE INVENTION

One or more embodiments of the present invention relates to unification of a solid-phase extraction column and a capillary for isoelectric focusing. One or more embodiments of the present invention provide a capillary device for separation and analysis, a microfluidic chip for separation and analysis, an analysis method for proteins and peptides, an electrophoresis instrument, and a microfluidic chip electrophoresis instrument, each of which comprises the following.

(1) A capillary device for separation and analysis comprising a capillary for isoelectric focusing and a solid-phase extraction column directly connected to said capillary for isoelectric focusing as a single entity.

(2) Said, above as (1), capillary device for separation and analysis in which hydrophilic polymer is bound to the inner wall of said capillary for isoelectric focusing.

(3) Said, above as (1) or (2), capillary device for separation and analysis in which said solid-phase extraction column comprises an affinity chromatography adsorbent, an ion-exchange chromatography adsorbent, or a hydrophobic chromatography adsorbent.

(4) Said, above as one of (1)~(3), capillary device for separation and analysis in which electroosmosis generated in the solid-phase extraction column is reduced by introducing a dissociable group having an electric charge in said solid-phase extraction column.

(5) A microfluidic chip for separation and analysis comprising a functionally equivalent structure of the capillary device for separation and analysis described in one of (1)~(4).

(6) A method for analyzing a protein or a peptide using the capillary device for separation and analysis described in one of (1)~(4) comprising the steps of:
introducing a sample containing a target protein or peptide into the solid-phase extraction column to allow the target protein or peptide to be adsorbed on the solid-phase extraction column, as Step 1;
eluting the target protein or peptide adsorbed on said solid-phase extraction column into the capillary device for separation and analysis, as Step 2;
focusing said eluted target protein or peptide in said capillary for isoelectric focusing by applying voltage on said capillary device for separation and analysis, as Step 3; and detecting said target protein or peptide after focusing, as Step 5.

(7) A method for analyzing a protein or a peptide described above in (6) comprising the step of controlling electroosmosis generated in said solid-phase extraction column by regulating the pressure difference between both ends of said capillary device for separation and analysis throughout said Step 3 and said Step 5, as Step 4.

(8) An electrophoresis instrument comprising the capillary device for separation and analysis described above in one of (1)~(4) and a detection apparatus having one or more boundary detectors that detects the boundary between two or more types of solution in the capillary device for separation and analysis.

(9) The electrophoresis instrument described above in (8) wherein said boundary detector is a boundary detector detecting the boundary between an injected sample solution and other solution.

(10) The electrophoresis instrument described above in (8) or (9) wherein said boundary detector is a boundary detector detecting the boundary between a carrier ampholyte solution and an eluent or an electrode solution.
(11) The electrophoresis instrument described above in (8)~(10) wherein said boundary detector is a contact-less or contact electric conductivity detector, a refractive index detector, an absorbance detector, a fluorescence detector, or a light-scattering detector.
(12) The electrophoresis instrument described above in (8)~(11) wherein said detection apparatus has a sample detector detecting the sample separated by isoelectric focusing.
(13) The electrophoresis instrument described above in (8)~(12) wherein said capillary device for separation and analysis is arranged in an inverted U-shape.
(14) A microfluidic chip electrophoresis instrument for separation and analysis comprising a functionally equivalent structure of the electrophoresis instrument described above in one of (8)~(13).

One or more embodiments of the present invention allow easy removal of interfering substance in a sample and enables the separation and analysis of proteins and peptides based on the difference of isoelectric points in a highly sensitive and highly precise manner.

DETAILED DESCRIPTION

One or more embodiments of the claimed invention will be explained below while referring to figures.

<Capillary Device for Separation and Analysis>

Figure 1:
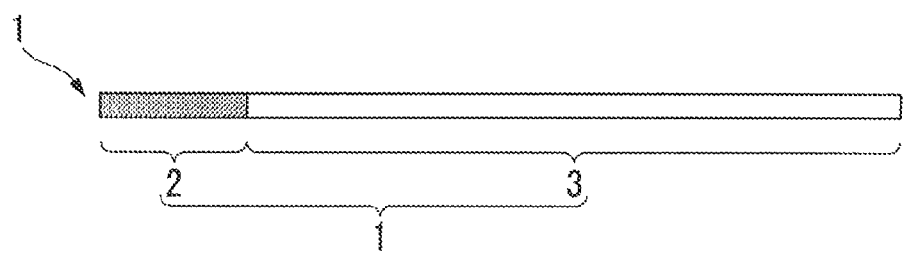
FIG. 1 shows a cross section of a capillary device for separation and analysis according to one or more embodiments of the present invention.

As shown in FIG. 1, a capillary device for separation and analysis 1 according to one or more embodiments of the present invention includes a solid-phase extraction column 2 and a capillary for isoelectric focusing 3 directly connected to the solid-phase extraction column 2 as a single entity. In one or more embodiments of the present invention, the phrase, "directly connected", means that the solid phase extraction column and the capillary for isoelectric focusing are connected not through other columns, capillaries, channels, or microfluidic channels, etc.

Capillary isoelectric focusing is a technique to separate components in a sample based on the difference of isoelectric points by applying voltage after introducing carrier ampholytes, a mixture of ampholytes having various isoelectric points, and a sample of proteins, etc. to the capillary. For the sake of convenience, "a sample" is sometimes called "a protein" in the following, but a sample is not limited to a protein.

As a capillary used for the capillary device for separation and analysis 1, a fused-silica capillary is preferable from the view point of superior corrosion resistance, low electric conductivity, extremely high transparency, etc., but, not limited to it, other capillaries having equivalent or superior quality can be used.

The inner diameter of the capillary device for separation and analysis 1 is preferably in a range of 1~500 μm. Being the inner diameter of a capillary device for separation and analysis in that range, dissipation of Joule heat produced by application of voltage is fast, and application of high voltage is possible. Consequently, very rapid separation with small amount of a sample is possible.

The inner wall of the capillary for isoelectric focusing 3 is preferably coated with a hydrophilic polymer in a viewpoint to reduce adsorption of proteins or peptides and electroosmotic flow being originated from the presence of silanol group on the inner wall of fused silica. As a hydrophilic polymer, cellulose derivatives such as hydroxyethyl cellulose, polyethylene glycol, polypropylene glycol, polyacrylamide, polydimethylacrylamide, polydiethylacrylamide, polyvinylpyrrolidone, polyethyleneoxide, polyvinyl alcohol, polyols (polyglycerin), dextran, agarose, etc. can be listed. The coating can be achieved by either of physical adsorption or chemical bonding. For example, a hydrophilic polymer can be bound on the inner wall of a capillary physically or chemically in advance, or a hydrophilic polymer can be used by adding it in a carrier ampholyte solution (a separation medium) to be physically adsorbed on the inner wall of the capillary.

The solid-phase extraction column 2 is coupled directly to the capillary for isoelectric focusing 3, and, in a viewpoint of reversible adsorption and desorption of a specific target substance, to have an affinity chromatography adsorbent is preferable. In this case, a protein having an affinity to the affinity ligand on the solid-phase extraction column 2 is specifically captured. Elution from the solid phase can be achieved by competition with a free ligand, by pH change with acidification or alkalinization, or by denaturing of protein with urea at high concentration, etc.

In addition, a solid-phase extraction column 2 having an ion-exchange chromatography adsorbent, or a hydrophobic chromatography adsorbent is also preferable. Using an ion-exchange chromatography adsorbent, a protein having desired effective surface charge can be specifically captured on the solid phase. furthermore, by using a hydrophobic chromatography adsorbent, the target protein can be suitably captured on the solid phase by exploiting the interaction between the target protein and the ligand on the solid phase.

As the solid-phase adsorbent of the solid-phase extraction column 2, an inner wall of a capillary, a monolith column prepared by forming a porous gel through polymerization reaction, a packed column with a beaded solid phase, a porous membrane, etc., can be used.

The cross sectional area of the capillary for isoelectric focusing and that of the solid-phase extraction column are not necessarily the same, and can be optimized suitably. Furthermore, the solid-phase extraction column 2 and the capillary for isoelectric focusing 3 can be provided separately, and can be unified and used at the beginning of the operation or after completion of the solid-phase extraction step.

As a combination of a target molecule/an affinity ligand in the use of affinity chromatography adsorbents, biotin-binding proteins such as avidin and streptavidin/biotin, maltose-binding protein/maltose, G proteins/guanine nucleotides, oligo-histidine peptides/metal ions such as nickel or cobalt, glutathione-S-transferase/glutathione, DNA-binding proteins/DNA, antibody/antigen molecule (epitope), antigen molecule (epitope)/antibody, antibody/protein A, antibody/ protein G, antibody/protein L, lectin/sugar, calmodulin/ calmodulin-binding peptide, ATP-binding protein/ATP, or estradiol-binding protein/estradiol, etc., can be referred as examples.

Among them, as a combination of a target molecule/an affinity ligand, biotin-binding proteins such as avidin and streptavidin/biotin, oligo-histidine peptides/metal ions such as nickel or cobalt, antibody/antigen molecule (epitope), antigen molecule (epitope)/antibody, antibody/protein A, antibody/protein G, antibody/protein L, lectin/sugar, etc. are preferable.

According to one or more embodiments of the present invention, in the capillary device for separation and analysis 1, the capillary for isoelectric focusing 3 and the solid-phase extraction column 2 is directly connected, and, thus, the device allows removal of highly abundant salts and proteins in a sample and analysis of a low concentration protein with isoelectric focusing.

Also, the capillary device for separation and analysis concentrates a target protein or peptide in the solid-phase extraction column 2, and, therefore, detection sensitivity can be drastically improved by increasing the amount of a sample applied on the solid-phase extraction column 2.

<Microfluidic Chip for Separation and Analysis>

In one or more embodiments of the present invention, the microfluidic chip for separation and analysis has a structure that is equivalent to that of the capillary device for separation and analysis above described. Namely, this microfluidic chip for separation and analysis has at least a channel for isoelectric focusing and a solid-phase extraction column that is directly connected to the channel.

Figure 2:
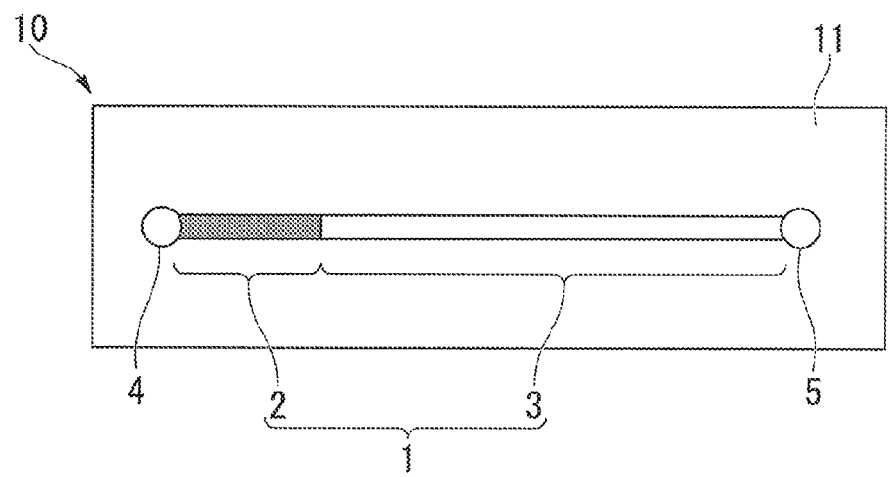
FIG. 2 shows a cross section of a microfluidic chip for separation and analysis according to one or more embodiments of the present invention.

As depicted in FIG. 2, the microfluidic chip for separation and analysis 10 is provided with a substrate 11, in which a solid-phase extraction column 2; a channel for isoelectric focusing 3; an electrode-solution reservoir for electrode solution 4; and another electrode-solution reservoir for another electrode solution 5 are fabricated.

As the material for the substrate 11, for example, plastic materials, glass, silica, quartz, photosetting resin, thermosetting resin, silicone, etc. can be referred.

Electrodes, omitted in FIG. 2, for electrophoresis can be equipped in each reservoir (electrode solution reservoir 4 and electrode solution reservoir 5) beforehand by, for example, spattering at each reservoir region on the substrate, or can be inserted into each reservoir on the substrate 11 from outside of the substrate 11 with a mechanism to insert electrodes.

Electrophoresis is carried out by applying a voltage between the electrodes. The voltage is preferably a DC voltage.

In one or more embodiments of the present invention, the microfluidic chip for separation and analysis 10 can have a mechanism to apply voltage and also a detection apparatus (omitted in FIG. 2) to detect the boundary of 2 types of solutions injected serially in the channel and a detection apparatus (omitted in FIG. 2) to detect a target protein or peptide.

As the detection apparatus, an electric conductivity detector or an optical detector, such as for refractive index, light scattering, UV adsorption, and fluorescence is preferable. The optical detection apparatus is provided with a light source and a detector. As the light source, laser, an LED and a lamp can be used, and, for the detector, a photomultiplier tube, a photo diode, an avalanche photo diode, a multipixel photo detector, and CCD camera can be used.

In one or more embodiments of the present invention, the microfluidic chip for separation and analysis 10 is a chip version of the capillary device for separation and analysis, and, thus, allows easy operation of the highly sensitive analysis of protein and peptide.

<Analysis Method for Proteins and Peptides>

In one or more embodiments of the present invention, the analysis method for proteins and peptides is the analysis method for proteins and peptides using the capillary device for separation and analysis, including the following steps.

Step 1: The sample containing a target protein or peptide is introduced into the capillary device for separation and analysis, and the target protein or peptide is adsorbed on the solid-phase extraction column.

Step 2: The target protein or peptide adsorbed on the solid-phase extraction column is eluted in the capillary device for separation and analysis.

Step 3: The eluted target protein or peptide is focused in the capillary for isoelectric focusing by applying voltage on the capillary device for separation and analysis.

Step 5: The target protein or peptide is detected.

Figure 3:
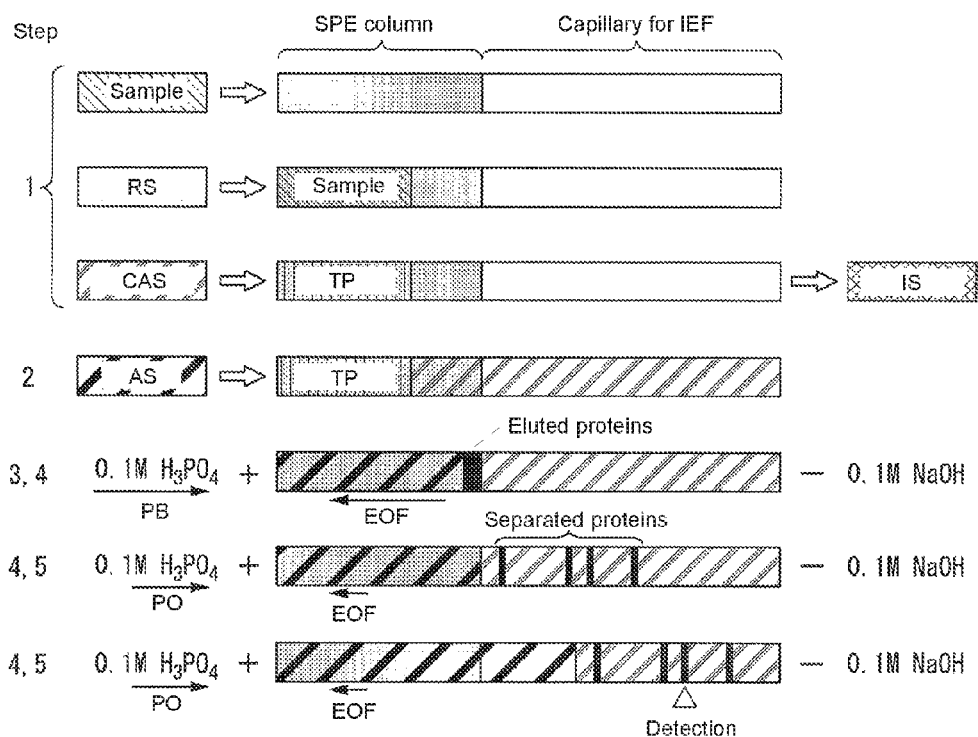
FIG. 3 shows explanation of an analysis method for separation and analysis according to one or more embodiments of the present invention.

Referring to FIG. 3, the analysis method for proteins and peptides in one or more embodiments of the present invention is explained below.

[Step 1]

In Step 1, a sample containing a target protein or peptide is introduced into the solid-phase extraction column. The target protein or peptide is specifically adsorbed on the solid-phase extraction column owing to the affinity of the solid-phase extraction column to the target protein or peptide.

If necessary, the solid-phase extraction column is rinsed. Unnecessary highly abundant proteins or interfering substances such as salts are removed from the target protein or peptide by introducing an appropriate buffer solution into the capillary device for separation and analysis.

The capillary device for separation and analysis is filled with a carrier ampholyte solution. It is preferable that the capillary for isoelectric focusing is filled with a carrier ampholyte solution including multiple ampholytes having both acidic and basic dissociation groups to form a pH gradient on application of voltage.

The range of the pH gradient formed with the carrier ampholyte solution can be selected to include the isoelectric point of the target protein or peptide. The anode vessel is filled with an anode solution containing acid such as phosphoric acid, and the cathode vessel is filled with a cathode solution containing base such as sodium hydroxide.

[Step 2]

In Step 2, the target protein or peptide adsorbed on the solid-phase extraction column is eluted. The method of elution is not limited in particular, and several methods can be listed, such as, the method of competition with a free ligand introduced into the solid-phase extraction column, the method of elution by acidification with the introduction of acid solution, the method of elution by alkalinization with the introduction of base solution, and the method of elution by introducing a denaturant such as urea at high concentration, etc.

[Step 3]

In Step 3, voltage is applied on the capillary device for separation and analysis, and the eluted the protein or peptide is focused (is separated, migrates) in the capillary for isoelectric focusing.

The range of applied voltage is preferably 100~1000 V per 1 cm of the length of the capillary for isoelectric focusing. During electrophoresis, cooling can be carried out to exclude the influence of Joule heat with, for example, an external circulation of cooling solvent, an air flow, and a peltier module, etc. Application of voltage forms a pH gradient owing to the carrier ampholyte in the capillary for isoelectric focusing. Since proteins and peptides are ampholytes, and their isoelectric points differ depending on the kind and number of the dissociation groups on the side chain of amino acids forming a peptide, the proteins and peptides present in the capillary device for separation and analysis are focused at specific positions of pH that are the same as their isoelectric points.

In the case of the target proteins are eluted by alkalinization in Step 2, isoelectric focusing should be performed with an inverted polarity.

In the case of the target proteins are eluted by competition or denaturation in Step 2, a carrier ampholyte solution containing a competing substance or denaturant should be introduced into the solid-phase extraction column, and, then, the section of the solid-phase extraction column should be filled with an anode solution or a cathode solution before initiation of isoelectric focusing. When the solid-phase extraction column is filled with an anode solution, the side of the solid-phase extraction column should be anode. When the solid-phase extraction column is filled with a cathode solution, the side of the solid-phase extraction column should be cathode.

[Step 4]

In the present embodiment, it is preferable to have Step 4 wherein the electroosmosis generated in the solid phase extraction column is controlled by regulating the pressure difference between both ends of the capillary device for separation and analysis throughout the whole process of Step 3 and 5.

In Step 4, if necessary, the electroosmosis generated in the solid-phase extraction device is controlled by regulating the pressure difference between both ends of the capillary device for separation and analysis. As an example, a voltage is applied with the side of the solid-phase extraction column immersed in an anode solution, and the side of the capillary for isoelectric focusing immersed in a cathode solution. The section of the solid-phase extraction column is probably charged positive by acidification. In that case, electroosmosis toward the anode should be generated depending on the electric conductivity of the anode solution, and the pH gradient containing the target protein or peptide dislocates as a whole toward the anode.

However, by applying a suitable pressure at the anodic end in Step 4, this flow produced by electroosmosis can be substantially cancelled and focusing by isoelectric focusing can be achieved in the capillary for isoelectric focusing. The regulation of the pressure difference between both ends of the capillary device for separation and analysis can also be carried out using hydrostatic pressure.

In place of Step 4, it is also preferable to control electroosmosis generated in the solid-phase extraction column by attaching electric charges unrelated to the solid-phase extraction to the solid-phase extraction adsorbent beforehand.

For example, in the case of the use of acid solution as an eluent in Step 2, the solid-phase adsorbent is positively charged and electroosmotic flow toward the anode should be generated in the solid-phase extraction column. This electroosmotic flow can be controlled by regulating the pressure difference as mentioned above in Step 4, and the generation of the electroosmotic flow by acidification can also be controlled by attaching beforehand the negative charges that balance with the positive charges taken by the solid-phase extraction adsorbent as the acidification.

The method to add electric charge is not limited in a particular way. As an example, when acid solution is used to fill the solid-phase extraction column, by introducing a strongly acidic dissociation group, such as sulfonic acid group, in the solid-phase extraction adsorbent in advance, the effective electric charge of the solid-phase extraction column can be kept at zero, even when the solid-phase extraction column is filled with an acid solution to elute the target protein or peptide captured in the solid-phase extraction adsorbent. In this way, the generation of electroosmotic flow is reduced, and the focusing by isoelectric focusing can be achieved in the capillary for isoelectric focusing. Furthermore, by reducing the generation of electroosmotic flow, the influx of an alkaline cathode solution, which can affect the inner coating of the capillary for isoelectric focusing, can be prevented.

[Step 5]

In Step 5, the target protein or peptide is detected after focusing. As an example, the signal from the label that was attached in advance to the target protein or peptide is captured.

In the case of the use of a fluorescent dye as a label, the excitation light that corresponds to the excitation wave length of the fluorescent dye is irradiated, and the fluorescence emitted from the fluorescent dye is captured. As an excitation light source, laser, an LED, a lamp can be used, and, if necessary, to irradiate only with the light of an excitation wave length, an optical filter, such as a band pass filter, is used.

For capturing of fluorescence, for example, a photo multiplier tube, a photo diode, an avalanche photo diode, a multipixel light detector, and a CCD camera, etc. can be used. To detect the light corresponding to the fluorescence wave length of a fluorescent dye, the use of optical filters, such as a band pass filter and notch filter, is preferable. Every possible combination of any light source and any detector other than those described above can also be used.

The measurement can be performed by scanning the capillary using a scanning detector, or by detection with a fixed-type detector. An imaging detector such as a CCD camera can also be used. When a fixed-type detector is used, the detection is preferably carried out by dislocating the whole pH gradient including the focused target protein or peptide against the fixed-type detector by regulating the pressure difference between both ends of the capillary device for separation and analysis. The dislocation of the whole pH gradient can also be carried out by the method to let the focused proteins migrate by electrophoresis toward cathode through acidification of the whole pH gradient by the addition of, for example, chloride ion in the cathode solution. The dislocation by electrophoresis can also be done toward the opposite direction, to the anode, by adding, for example, sodium ion in the anode solution.

The proteins or peptides in the capillary device for separation and analysis focus at the positions with the same pH as their isoelectric points, and are separated. The amount of the target protein or peptide is calculated based on the amount of signal from the label present at these positions of isoelectric point.

In addition, in Step 5, in place of optical detection using a fluorescent dye described above, the measurement can be performed using UV adsorption or electric conductivity at the position of the isoelectric points of the target protein and peptide.

Using the analysis method of protein and peptide in one or more embodiments of the present invention, the capillary device for separation and analysis can capture almost all target molecules in a sample on the solid-phase extraction column, and, thus, easily allows the highly sensitive analysis of proteins and peptides.

<Electrophoresis Instrument>

In one or more embodiments of the present invention, the electrophoresis instrument is an instrument including the capillary device for separation and analysis, and the detection apparatus having one or more boundary detector detecting the boundary between two or more type of solution present in the capillary device for separation and analysis.

Figure 5:
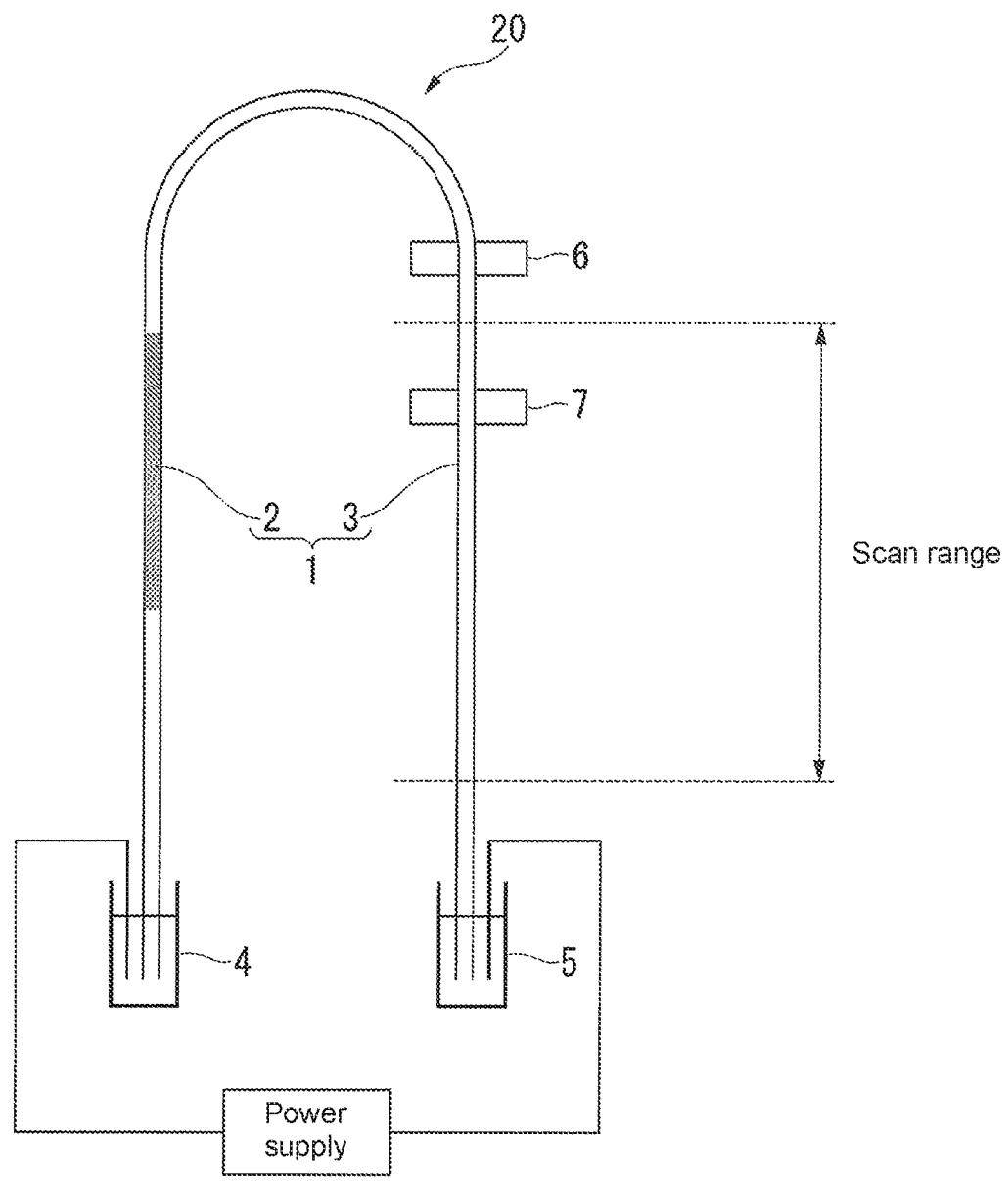
FIG. 5 is a schematic drawing of an electrophoresis instrument according to one or more embodiments of the present invention.

The electrophoresis instrument, 20, presented in FIG. 5, includes, as an example, the capillary device for separation and analysis, 1, having the solid-phase extraction column, 2 and the capillary for isoelectric focusing, 3; the electrode solution reservoir, 4; the electrode solution reservoir, 5; and the detection apparatus having the boundary detector, 6, and the protein detector, 7.

The electrophoresis instrument further includes the electrode solution reservoir 4 having an anode, the electrode solution reservoir 5 having a cathode, and the electrodes being connected to an electric power supply applying voltage between the electrodes during electrophoresis.

In the electrophoresis instrument 20 presented in FIG. 5, the capillary device for separation and analysis 1 is arranged in an inverted U-shape as one example of preferable arrangements; the solid-phase extraction column 2 is placed at the side of the electrode solution reservoir 4 and the anode; and the capillary for isoelectric focusing 3 is placed at the side of the electrode solution reservoir 5 and the cathode.

The detection apparatus has a boundary detector, 6, that detects a boundary between two or more types of solutions present in the capillary device for separation and analysis.

For example, to perform isoelectric focusing, the boundary detector 6 in FIG. 5 can detect the boundary between the carrier ampholyte solution filled in the capillary for isoelectric focusing and the eluent or the electrode solution that is introduced to elute the target protein or peptide from the solid-phase extraction column 2.

In the case of a commonly used open-tubular capillary, the flow speed of a solution in the capillary and the boundary of solutions can be calculated and regulated based on the pressure applied. When the capillary for solid-phase extraction, however, has a structure inside such as packing material, pinpointing the position of a boundary of solutions could be difficult, since the flow resistance could change due to the packing state of the packing material or clogging with particulate matter in the sample, etc.

On the other hand, with the boundary detector 6 as this embodiment, the boundary between the carrier ampholyte solution and the eluent or the electrode solution can be detected even when the relationship between the pressure and the flux is not known, and the separation and analysis of the target protein or peptide can be carried out precisely and efficiently by adjusting the boundary to an appropriate position.

The electrophoresis instrument 20 can also have other boundary detectors (omitted in FIG. 5) in addition to the boundary detector 6. With multiple boundary detectors, the change of the flux of solution in the process of injection can be detected and the occurrence of problems can be sensed, such as the contamination of particulate materials in the injected solutions.

As the other use of the boundary detector, the detection of the boundary between the sample solution injected into the solid-phase extraction column 2 and the solution filled in the capillary device for separation and analysis 1 before the injection of the sample solution. Detection of the boundary allows the measurement of the injected volume of a sample and, thus, enables quantitative separation and analysis.

As the boundary detectors (boundary detector 6, and other boundary detectors), a contactless or contact electric conductivity detector, a refractive index detector, an absorbance detector, a fluorescence detector, or a light-scattering detector is preferable.

Among them, a contactless electric conductivity detector is especially preferable because of the easiness of detection and the flexibility in the arrangement without restriction to the material or the shape of the capillary device for separation and analysis. For example, in the detection of the boundary between a carrier ampholyte solution and an electrode solution, the boundary can be easily detected, since the electric conductivity of a carrier ampholyte solution is generally low, and the electric conductivity of an electrode solution is generally high.

The above described detection apparatus further has a protein detector (a sample detector) 7 that detects the sample separated by isoelectric focusing. The protein detector 7 is for detection of the target protein or peptide focused by isoelectric focusing, and the scanning detector, a fixed-type detector, and an imaging detector, etc., above described, can be used as the detector.

The electrophoresis instrument, including a mechanism that regulate the pressure difference between both ends of the capillary device for separation and analysis, can control the injection of a solution into the capillary device and control the flow of the solution in the capillary for isoelectric focusing produced by the electroosmosis generated in the solid-phase extraction adsorbent. In the focusing (separation, migration) by isoelectric focusing, it is preferable to minimize the influence of electroosmosis generated in the solid-phase extraction adsorbent by regulating pressure. This condition can be realized, for example, by starting isoelectric focusing placing the boundary between a carrier ampholyte solution and an anode solution at the position of the boundary detector 6, and, under continuous monitoring of the boundary, by controlling dynamically the pressure in order that the boundary does not move from the position by the influence of electroosmosis generated in the solid-phase extraction adsorbent.

According to one or more embodiments of the present invention, the electrophoresis instrument can make maximum use of the capillary device for separation and analysis, and, thus, can perform the analysis and detection of proteins and peptides highly sensitively and easily.

<Microfluidic Chip Electrophoresis Instrument for Separation and Analysis>

In one or more embodiments of the present invention, the microfluidic chip electrophoresis instrument for separation and analysis is furnished with a structure that is functionally equivalent to the electrophoresis instrument as described above.

This microfluidic chip electrophoresis instrument for separation and analysis can perform the analysis and detection of proteins and peptides highly sensitively and easily as well as the electrophoresis instrument.

Example of Embodiment

This invention is explained in more detail with an example of embodiment and, however, is not limited to this example.

A fused-silica capillary (50 μm i.d., 365 μm o.d., 70 cm in length) was filled with a mixture of 3-methacryloxypropyltrimethoxysilane/acetone/acetic acid (10/45/45, v/v/v) and left over night at room temperature to let methacryloxypropyl group bind to the inner wall.

After the capillary was rinsed and dried, the outer wall at 40 cm from an end was marked with a felt-lip pen. A polymerization solution of dimethylacrylamide was injected from the end of the longer segment of the capillary divided by the mark until the front of the solution reached the mark point. The both ends were sealed by rubber septa, and the capillary was left at 50° C. for 2 hours to induce copolymerization of dimethylacrylamide and methacrylate bound on the inner wall beforehand in order that the resulting polydimethylacrylamide could bind on the inner wall and should reduce electroosmosis and adsorption of proteins.

After the capillary was rinsed and dried, a polymerization solution of glycidylmethacrylate was injected from the end of the shorter segment of the capillary until the front of the solution reached the mark point. The both ends were sealed by rubber septa, and the capillary was left over night at 50° C. to induce copolymerization of glycidylmethacrylate and methacrylate bound on the inner wall beforehand in order that the resulting polyglycidylmethacrylate could bind on the inner wall.

After rinsing and drying, only the segment of the capillary bound with polyglycidylmethacrylate was filled with sodium iminodiacetate solution (pH 9.0) and left at 50° C. for 1.6 hours to let iminodiacetate bind. The capillary was cut at 20 cm from the mark on the side bound with iminodiacetate and at 30 cm from the mark on the side bound with polydimethylacrylamide. The capillary with a total length of 50 cm was used as a capillary device for separation and analysis.

This capillary device for separation and analysis was installed in a full automatic capillary electrophoresis instrument, Beckman-Coulter P/ACE MDQ, with the iminodiacetate-bound side at the anode. Detection was carried out at 10 cm from the cathodic end of the capillary device with fluorescence at around 590 nm using 532 nm laser for excitation.

To this capillary device for separation and analysis, 20 mM Tris-hydrochloric acid buffer (pH 7.4) containing 0.5 M sodium chloride was injected from the anodic end at a pressure of 2 psi for 1 min as an equilibration buffer. A 100 mM nickel chloride solution was then injected at 2 psi for 1 min to let nickel ion bind to iminodiacetate to form a solid-phase extraction column targeting at the proteins having hexahistidine tag. The following injections were always done from anodic side to cathodic side.

To remove excessive nickel ion, the capillary was rinsed by injecting 20 mM Tris-hydrochloric acid buffer (pH 7.4) containing 10 mM imidazole and 0.5 M sodium chloride as a rinse solution at 2 psi for 1 min.

A sample containing 20 nM labeled Fab, which was obtained by fluorescence-labeling and purification of recombinant mouse Fab antibody fragment to have an isoelectric point of 7.70, in 100 mM Tris-hydrochloric acid buffer (containing 0.1% Tween 20) was injected at 0.5 psi for 2 min (corresponding to a sample plug of 7.5 cm in length), and Fab was adsorbed on the solid-phase extraction column. The rinse solution mentioned above was, then, injected at 2 psi for 1 min, and a carrier ampholyte solution (2.5% (v/v) Pharmalyte 3-10, 0.1% acetic acid, 0.6% tetramethylethylenediamine) containing 4 kinds of fluorescence-labeled peptides as isoelectric point markers at 2.5 nM each was injected at 40 psi for 0.3 min to substitute the inside of the capillary device with the solution containing isoelectric point markers and carrier ampholyte.

Phosphoric acid at 100 mM as an eluent and also as an anode solution was injected at 2 psi for 1.3 min to fill the solid-phase extraction column part with it and to elute the bound Fab on the solid-phase extraction column. Under this condition, the sample Fab should have been eluted at around the boundary between the solid-phase extraction column and the capillary for isoelectric focusing. The nickel ion bound to the iminodiacetate is also detached and ionization of the carboxyl group of iminodiacetate is suppressed. The positive charge on the imino group of iminodiacetate stays there and, thus, the solid-phase extraction column became positively charged.

A constant DC voltage of 25 kV was applied with a maximum limit of electric current of 20 μA using 100 mM phosphoric acid as anode solution and 100 mM sodium hydroxide as cathode solution. To reduce electroosmotic flow generated in the solid-phase extraction column, a pressure of 0.2 psi was applied at the anodic end.

Electroosmosis toward anode was generated, since the solid-phase extraction column is positively charged. At the beginning of electrophoresis, the voltage drop in the part of the solid-phase extraction column was large, and consequently electroosmosis was also large. As the progress of formation of a pH gradient having low electric conductivity and the consequent increase of the voltage drop in the pH gradient, the voltage drop in the solid-phase extraction column gradually decreased, and consequently the electroosmosis also decreased.

The pressure control system of the capillary electrophoresis instrument used in this experiment has a minimum pressure increment setting by 0.1 psi, and 0.1 psi is the minimum pressure setting. The pressure applied at the anodic end was set at 0.2 psi for the first 2 min period from the initiation of the focusing by electrophoresis, and at 0.1 psi thereafter. This pressure program could almost suppressed the dislocation of the pH gradient toward the anode in the early period of electrophoresis. By keeping the pressure of 0.1 psi and advancing focusing, the detection of the whole pH gradient after completion of focusing was possible through gradual dislocation of the pH gradient toward a detection point. The Fab of an isoelectric point of 7.70 was detected at a position of 22.7 min after start of analysis. This position was reasonable in referring to the separation result of the isoelectric point markers separated simultaneously.

Figure 4:
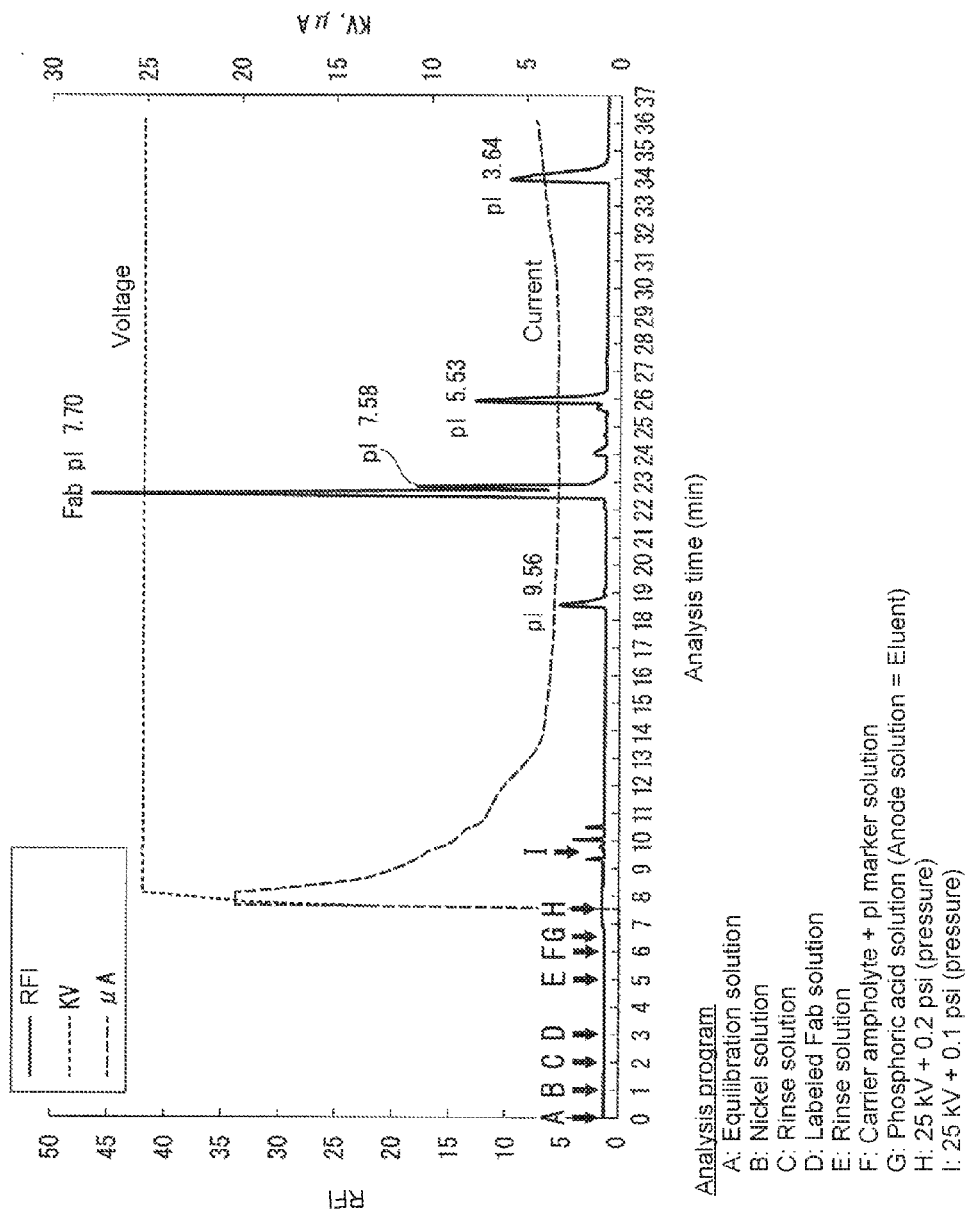
FIG. 4 shows a result of an embodiment according to the present invention.

As shown in FIG. 4, a His-tagged fluorescence-labeled recombinant Fab having a specified pI value was detected at high sensitivity.

While the invention has been described with respect to a limited number of embodiments, those skilled in the art, having benefit of this disclosure, will appreciate that other embodiments can be devised which do not depart from the scope of the invention as disclosed herein.

EXPLANATIONS OF SYMBOLS

1 Capillary device for separation and analysis
2 Solid-phase extraction column
3 Capillary for isoelectric focusing
4 Electrode solution reservoir
5 Electrode solution reservoir
6 Boundary detector
7 Protein detector (Sample detector)
10 Micro fluidic chip for separation and analysis
11 Substrate
12 Electrophoresis instrument

What is claimed is:

1. A method for analyzing a target protein and a target peptide comprising the steps of:
   providing an electrophoresis instrument that includes a capillary for isoelectric focusing and a solid-phase extraction column connected with one another in series;
   introducing a sample containing a target protein or peptide into the solid-phase extraction column to let the target protein or peptide be adsorbed on said column;
   after the step of introducing the sample, filling the capillary and the solid phase extraction column with a solution containing carrier ampholyte; and
   after the step of filling the capillary and the solid phase extraction column, injecting electrode solution into the solid-phase extraction column such that the solid-phase extraction column is filled with the electrode solution and the capillary for isoelectric focusing is filled with the solution containing carrier ampholyte;
   thereby starting separation of the target protein and peptide adsorbed on the solid-phase extraction column by isoelectric focusing in the capillary.

2. The method for analyzing a target protein and a target peptide claimed in claim 1, comprising:
   introducing electric charges in said solid-phase extraction column, thereby reducing electroosmotic flow produced in said solid-phase extraction column.

3. The method for analyzing a protein and a peptide claimed in claim 1, further comprising:
   detecting one or more boundaries between two or more types of solutions present in said capillary device for separation and analysis in the course of the steps of analysis.

4. The method for analyzing a protein and a peptide claimed in claim 3,
   wherein said boundary detector is a boundary detector detecting the boundary between an injected sample solution and other solution.

5. The method for analyzing a protein and a peptide claimed in claim 3,
   wherein said boundary detector is a boundary detector detecting the boundary between the carrier ampholyte solution or the eluent containing carrier ampholyte and the electrode solution or the acid or base solution.

6. The method for analyzing a protein and a peptide claimed in claim 3, wherein said boundary detector is a contactless or contact electric conductivity detector, a refractive index detector, an absorbance detector, a fluorescence detector, or a light-scattering detector.

7. The method for analyzing a protein and a peptide claimed in claim 3, wherein said detection instrument further has a detector for the sample being separated by isoelectric focusing.

8. A method for analyzing a protein and a peptide comprising the steps of:
   providing a capillary for isoelectric focusing having chemically bonded or physically adsorbed hydrophilic polymer on an inner wall of said capillary;
   providing a capillary device for separation and analysis having said capillary and a solid-phase extraction column being unified as a single tube-like structure;
   providing an electrophoresis instrument having said capillary device and the mechanism regulating the pressure difference at both ends of said capillary device;
   introducing a sample containing a target protein or peptide into the solid-phase extraction column to let the target protein or peptide be adsorbed on said column, and filling said capillary device with a carrier ampholyte solution;
   starting separation by capillary isoelectric focusing after eluting the target protein or peptide adsorbed on said solid-phase extraction column by filling the solid-phase extraction column with electrode solution or acid or base solution, or after firstly eluting the target protein or peptide with an eluting solution containing carrier ampholyte and secondly filling the solid-phase extraction column with electrode solution or acid or base solution;
   focusing said eluted target protein or peptide in said capillary for isoelectric focusing by applying a voltage on said capillary device for separation and analysis;
   detecting said target protein or peptide after the step of focusing; and
   further detecting one or more boundaries between two or more types of solutions present in said capillary device for separation and analysis in the course of the above steps of analysis.

9. The method for analyzing a protein and a peptide claimed in claim 8,
   wherein said boundary detector is a boundary detector detecting the boundary between an injected sample solution and other solution.

10. The method for analyzing a protein and a peptide claimed in claim 8,
    wherein said boundary detector is a boundary detector detecting the boundary between the carrier ampholyte solution or the eluent containing carrier ampholyte and the electrode solution or the acid or base solution.

11. The method for analyzing a protein and a peptide claimed in claim 8, wherein said boundary detector is a contactless or contact electric conductivity detector, a refractive index detector, an absorbance detector, a fluorescence detector, or a light-scattering detector.

12. The method for analyzing a protein and a peptide claimed in claim 8, wherein said detection instrument further has a detector for the sample being separated by isoelectric focusing.

13. The method for analyzing a protein and a peptide claimed in claim 8, wherein the separated sample is detectable by scanning at one of the straight segment of said capillary device for separation and analysis being installed in an inverted U-shaped arrangement.

* * * * *